(12) United States Patent
Sauer et al.

(10) Patent No.: US 8,517,930 B2
(45) Date of Patent: Aug. 27, 2013

(54) VALVE DEVICE FOR MEDICAL INSTRUMENTS

(75) Inventors: Michael Sauer, Tuttlingen (DE); Martin Oberlaender, Engen (DE); Elmar Teichtmann, Villingen-Schwenningen (DE)

(73) Assignee: Karl Storz GmbH & Co. KG (DE)

( * ) Notice: Subject to any disclaimer, the term of this patent is extended or adjusted under 35 U.S.C. 154(b) by 1636 days.

(21) Appl. No.: 11/517,987

(22) Filed: Sep. 8, 2006

(65) Prior Publication Data

US 2007/0073241 A1 Mar. 29, 2007

(30) Foreign Application Priority Data

Sep. 9, 2005 (DE) .......................... 10 2005 042 892

(51) Int. Cl.
*A61B 1/00* (2006.01)

(52) U.S. Cl.
USPC ........................................................ 600/184

(58) Field of Classification Search
USPC ............. 604/164.01, 164.02, 167.01, 167.03, 604/167.05; 606/108, 167; 251/162, 265, 251/264, 304, 305; 74/89.45; 600/184
See application file for complete search history.

(56) References Cited

U.S. PATENT DOCUMENTS

| | | | |
|---|---|---|---|
| 3,602,478 A * | 8/1971 | Cairns | 251/58 |
| 4,024,890 A * | 5/1977 | Yasuoka | 137/556.3 |
| 4,654,030 A | 3/1987 | Moll et al. | 604/165 |
| 6,793,194 B1 * | 9/2004 | Grinberg | 251/58 |
| 2005/0124932 A1 * | 6/2005 | Foster et al. | 604/99.04 |

FOREIGN PATENT DOCUMENTS

| | | |
|---|---|---|
| DE | 89 16 160 | 5/1994 |
| DE | 94 18 005 | 12/1994 |
| DE | 296 19 635 | 1/1997 |
| DE | 297 00 762 | 5/1998 |
| DE | 200 17 944 | 3/2001 |
| DE | 201 08 877 | 10/2001 |
| DE | 101 35 979 | 2/2003 |
| EP | 0 542 432 | 5/1993 |
| EP | 14 81 641 | 12/2004 |
| WO | WO 03/041598 | 5/2003 |

OTHER PUBLICATIONS

European Search Report, Nov. 27, 2006, 5 pages.
German Search Report, Aug. 16, 2006, 4 pages.

* cited by examiner

*Primary Examiner* — Thomas McEvoy
(74) *Attorney, Agent, or Firm* — St. Onge Steward Johnston & Reens LLC

(57) ABSTRACT

The invention relates to a valve device for medical instruments, in particular trocars, having a valve body configured as a flap for opening and closing an instrument and/or flow channel, which is positioned rotatably on a rotation axle positioned in a housing. To create a valve device, which combines simple and cost-effective structure with good cleaning properties, it is proposed with the invention that the rotation axle is configured in several components, such that the individual components of the rotation axle can be connected to one another by helical-shaped guide tracks.

17 Claims, 7 Drawing Sheets

VALVE DEVICE FOR MEDICAL INSTRUMENTS

FIELD OF THE INVENTION

The invention relates to a valve device for medical instruments, in particular trocars, having a valve body configured as a flap for opening and closing an instrument and/or flow channel that is positioned so that it can rotate on a rotation axle positioned in a housing.

BACKGROUND OF THE INVENTION

Valve devices of this type for medical instruments are used, for instance, in trocars. Trocars are used for inserting operating instruments for endoscopic operations, for instance into the abdominal cavity of a patient. For this purpose the trocar sleeve is placed on the abdominal surface, a trocar pin is inserted into the hollow instrument channel, an opening is made in the abdominal surface with the help of the trocar pin, and then the trocar sleeve is inserted into the abdominal area through the opening. The trocar pin can then be withdrawn again from the trocar sleeve.

Because it is common, with endoscopic operations of the abdominal area, to fill the abdominal area with gas for expanding the operating space and forming a pneumo-peritoneum, the hollow instrument channel of the trocar sleeve can be closed with a valve body so that the gas cannot escape from the abdominal area by way of the trocar sleeve when the instrument is removed. Valve bodies known in the art are configured in such a way that they are opened by an instrument that is inserted into the instrument channel and then close again independently when the instrument is removed.

A generic valve device for a medical instrument, namely a trocar, is known for instance from DE 297 00 762 U1. In this known trocar, the rotation axle that supports the valve body is configured as a U-shaped arched wire spring, by which the valve body is pre-tensioned in the closed position. The free ends of the spring are bent inward at a right angle at various points and secured in the housing in bore-holes arranged at intervals from one another. Because of the various lengths of the strands of the spring, the rotating of the valve body causes a tensing of the spring, so that it pressures the valve body in the direction toward the closed position. The configuration of the bore-holes for inserting the free ends of the spring makes it necessary to respect narrow tolerance values, so that the manufacture becomes labor-intensive and thus expensive. In addition this known valve device is very difficult to clean.

It is consequently the object of the invention to design a valve device for medical instruments of the aforementioned type in such a way that it is of simple, cost-effective construction and can easily be cleaned. The fulfillment of this object according to the invention is characterized in that the rotation axle is configured in several components, such that the individual components of the rotation axle can be connected to one another by means of helical-shaped guide tracks.

SUMMARY OF THE INVENTION

As a result of the inventive design of the rotation axle as a multi-partite spiral rod, on which the valve body is rotatably mounted, the structure is simple to manufacture and can be installed quickly and without complexity, while it also can be disassembled quickly and without problems for purposes of cleaning. In addition, easy rotation of the valve body is ensured by the spiral sections of the individual components of the rotation axle, which can be screwed into one another.

According to a practical embodiment of the invention, one component of the rotation axle can rotate exclusively around its longitudinal axis and cannot be mounted translationally in the housing, and the valve body is preferably non-rotatably mounted on this rotation axle component which can rotate exclusively around its longitudinal axis. Execution of a radial rotation movement of this rotation axle component, exclusively around its axle, ensures a non-jamming rotation of the valve body between the open position and the closed position and a constant precise positioning of the valve body on the insulating surface of the housing.

With a preferred embodiment of the invention it is proposed that the rotation axle consist of two components, such that one component can rotate exclusively around its longitudinal axis and is mounted so that it is not translational in the housing, and the other component is mounted in the housing so that it can slide axially exclusively in the longitudinal direction of the component and cannot rotate in the housing. Because the rotation axis consists of only two components, which can be connected to one another by helical-shaped guide tracks, the number of components is reduced to a minimum, which again has a positive effect on the assembly and disassembly of the valve device.

According to an alternative embodiment of the invention it is proposed that the rotation axle is mounted at least partly in an axle sleeve. The use of this axle sleeve allows, first, a lateral motion of the multi-part rotation axle and in addition facilitates the assembly and disassembly of the valve device because of the configuration of component sections that can be pre-assembled.

Moreover, with this embodiment the lubrication—between the component that can slide exclusively axially around its longitudinal direction and cannot rotate, and the component that can rotate exclusively around its longitudinal axis and cannot move translationally—is encapsulated apart from the flow channel.

In using the axle sleeve for mounting the rotation axle, it is advantageous to position the valve body on the axle sleeve in order to simplify the assembly and disassembly of the component groups. To transmit the rotary motion of the part of the rotation axis that can rotate exclusively around its longitudinal axis to the valve body mounted on the axle sleeve, it is proposed with the invention that the valve body and the axle sleeve should be essentially form-locked together and the part of the rotation axle that can rotate exclusively around its longitudinal axis and the axle sleeve should be connected together by material locking.

Alternatively to these preferred types of connection for transmitting the rotary motion of the part of the rotation axle that can rotate exclusively around its longitudinal axis to the valve body mounted on the axle sleeve, it is also possible of course to use all other combinations of linking types such as form-locking, material-locking, and or force-locking.

In using an inventive valve device in a trocar, for instance, to avoid having sensitive instrument points damaged because they must hit against the valve body when the instrument is inserted into the instrument channel and, in removing tissue sections, to avoid damage to the tissue sample from the valve flap or from grazing it by the forceps, it is further proposed with the invention that the valve body in addition should be moved into the open position by a manually actuated mechanism. By means of this mechanism it is now possible, rather than hitting against the valve body with the instrument that is inserted into the instrument channel, to open the valve body manually from outside, in order thus to avoid contact of the instrument point and/or of the tissue sample with the valve body.

According to a practical embodiment of the invention, this manually actuated mechanism is configured as a push-button that is in active connection with the part of the rotation axle that can slide axially exclusively in the longitudinal direction and cannot rotate. The push-button here preferably pre-tensioned by at least one spring element with respect to the part of the rotation axle that can slide axially and cannot rotate, in order to prevent, on the one hand, accidental opening of the valve body and, on the other hand, to pre-tension the valve body in the closed position.

The pre-tensioning of the at least one spring element can thus advantageously be adjusted by a tension nut that can be screwed onto a bearing bush of the housing in the area of the manually actuated mechanism.

In order, furthermore, to ensure that the part of the rotation axle that can slide axially exclusively in the longitudinal direction does not execute any rotary motion around its axis, this part of the rotation axle is prevented from rotation by means of a guide pin, such that the guide pin in the area of the manually actuated mechanism, for example in the tension nut, is mounted in a recess of the part of the rotation axle that can slide axially.

It is finally proposed with the invention that the part of the housing that bears the valve body and the rotation axle should form a separate valve carrier unit. This valve carrier unit, configured as a separate component, makes it possible to use the inventive valve device for other medical instruments and devices as well, for instance as an intermediary element to connect two instrument channels.

Further characteristics and advantages of the invention can be seen in reference to the annexed illustrations, in which two embodiments of an inventive valve device for medical instruments are presented merely in exemplary manner, without restricting the invention to these embodiments.

DETAILED DESCRIPTION OF THE INVENTION

Figure 1:
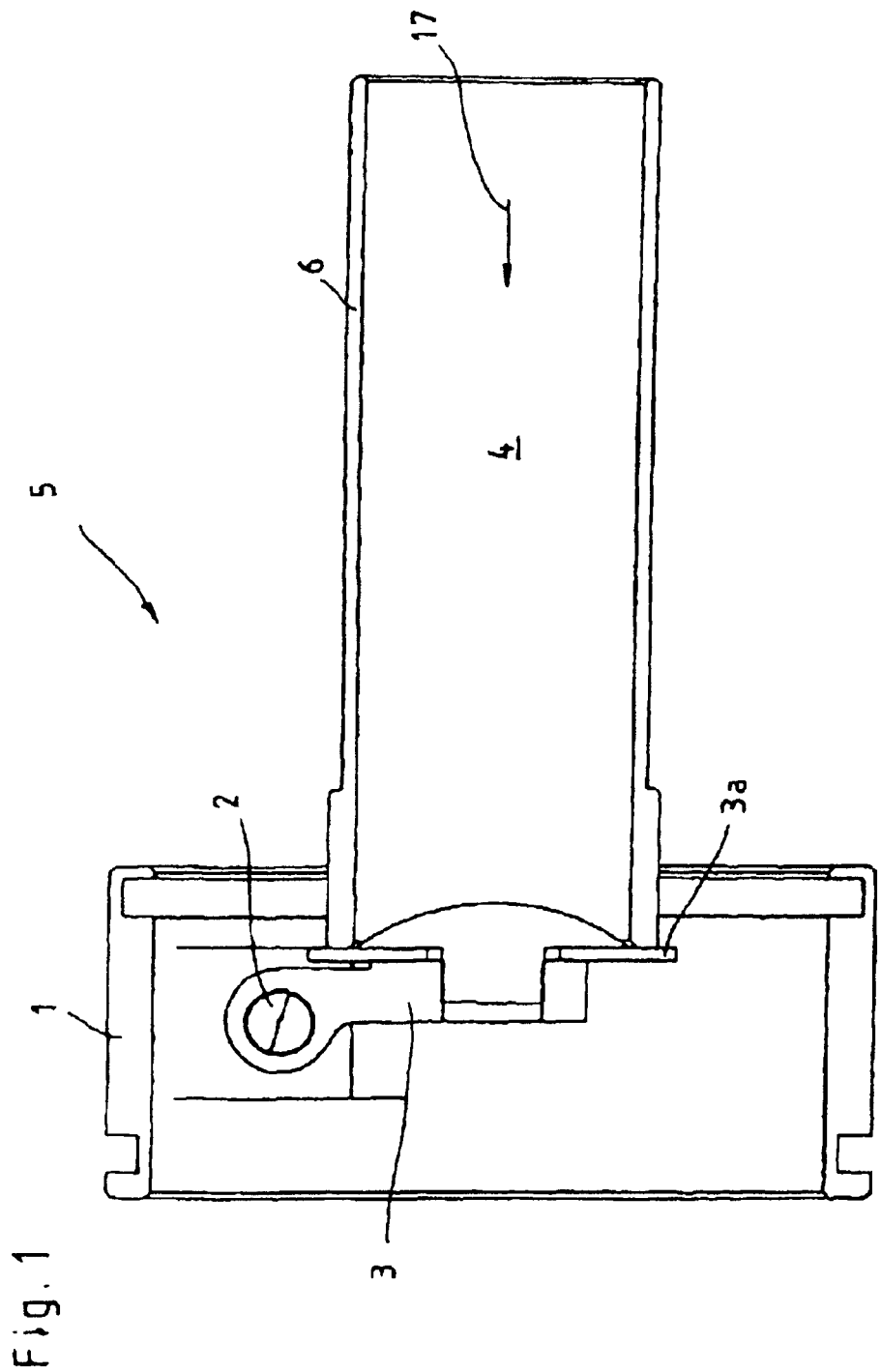
FIG. 1 shows a schematic side view of a valve device for medical instruments, mounted on a tubular channel.

The valve device for medical instruments illustrated in FIG. 1 consists essentially of a valve body 3, mounted in a housing 1 and rotatable on a rotation axle 2, by means of which an instrument channel and/or flow channel 4 can be closed and opened again. In the illustrated embodiment the valve body 3 is configured as a valve flap 3.

In the embodiment illustrated in FIG. 1 the rotation axle 2 with the valve body 3 mounted on it as well as the housing part 1 that bears the rotation axle 2 are configured as a separate valve carrier unit 5, which can be inserted as an independent component in various medical instruments. In the illustrated example, a tubular channel 6 is coupled onto the valve carrier unit 5 and its instrument and/or flow channel 4 can be closed by an insulating surface 3a of the valve body 3 configured as a flap.

The illustrated valve devices are used in particular with medical instruments configured as trocars. The hollow instrument channel 4 serves, with a trocar, to remove a trocar pin at the beginning of the operation, with which pin an aperture, for instance in the abdominal surface of the patient, is punctured. The trocar sleeve is then inserted into this aperture, and the trocar pin is then withdrawn again from the instrument channel 4. During the ensuing operation all sorts of endoscopic instruments can be introduced into the surgical area by way of the instrument channel 4. Because it is customary in endoscopic operations of the abdominal area to fill the patient's abdominal area with gas to expand the surgical area and to form a pneumo-peritoneum, the hollow instrument channel 4 of the trocar can be closed by the valve body 3 in order to prevent gas from escaping while an instrument is withdrawn from the instrument channel 4.

It is also possible, of course, to configure the hollow channel as a flow channel 4 for a liquid or gaseous medium, such that the valve body 3 then serves to prevent or else to release the passage of this medium.

Figure 2:
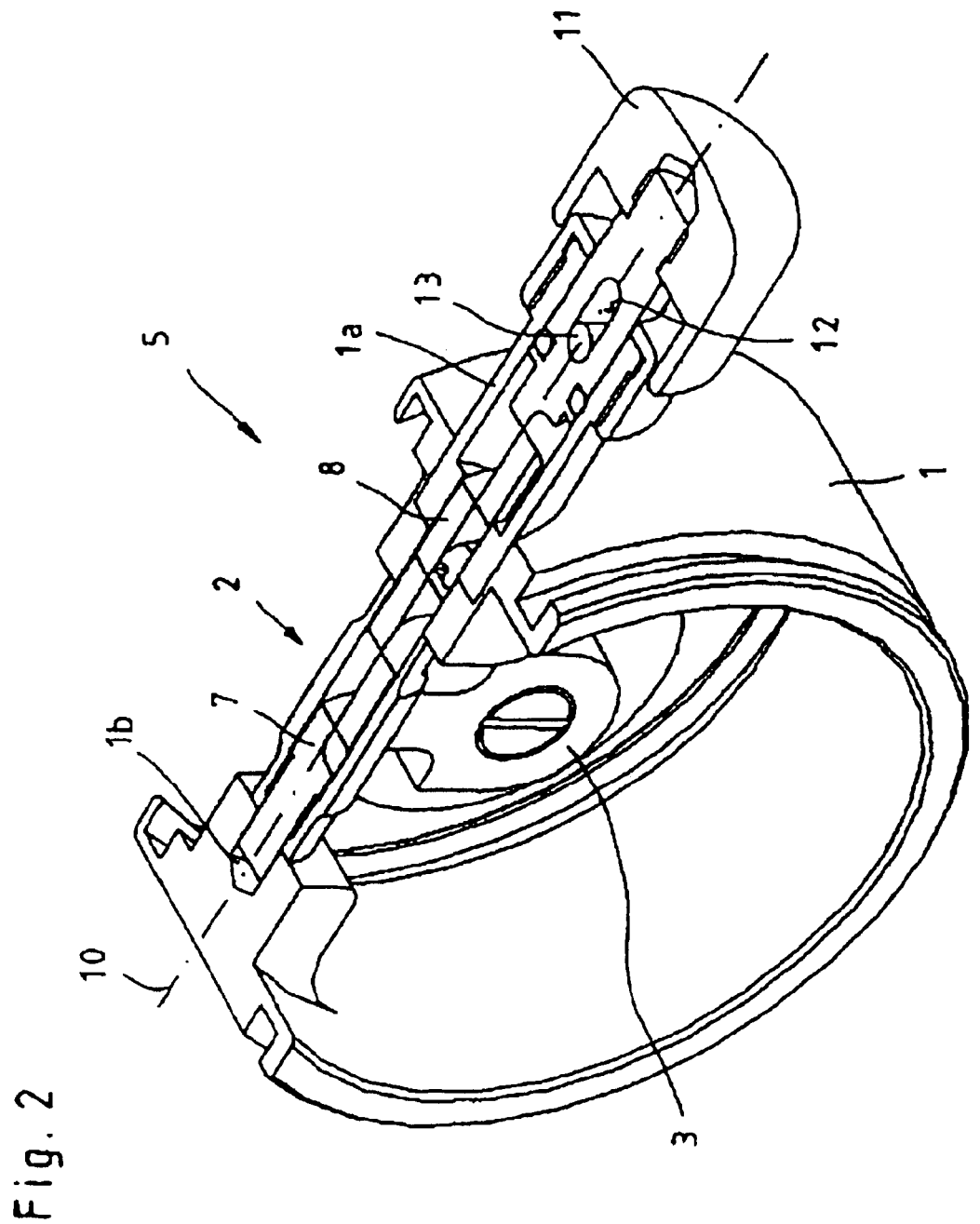
FIG. 2 shows a partly cut-out perspective view of the valve device according to FIG. 1, without a tubular channel connected, constituting a first embodiment of the invention.
Figure 3:
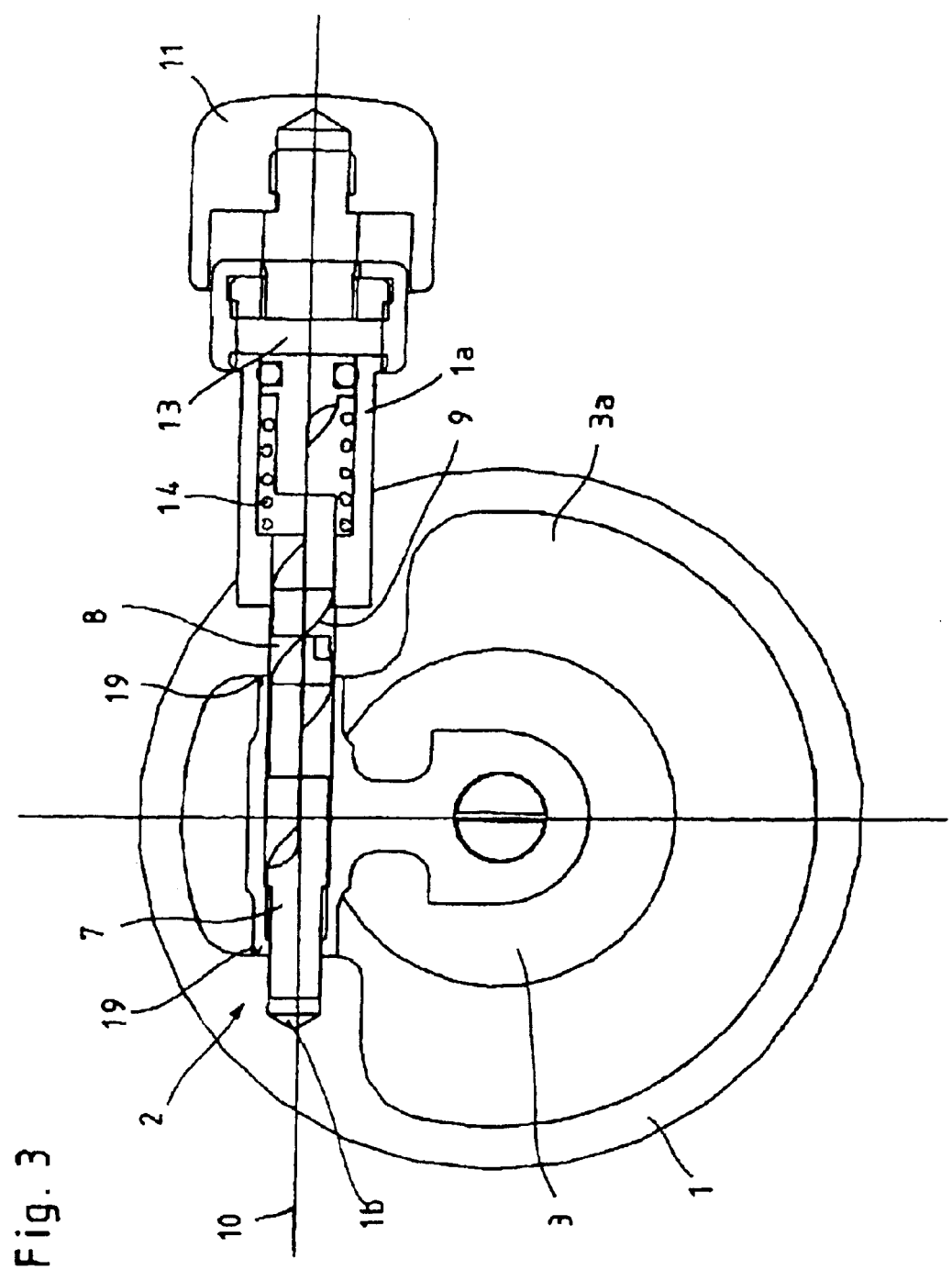
FIG. 3 shows a partly cut-out front view of the depiction according to FIG. 2.
Figure 4:
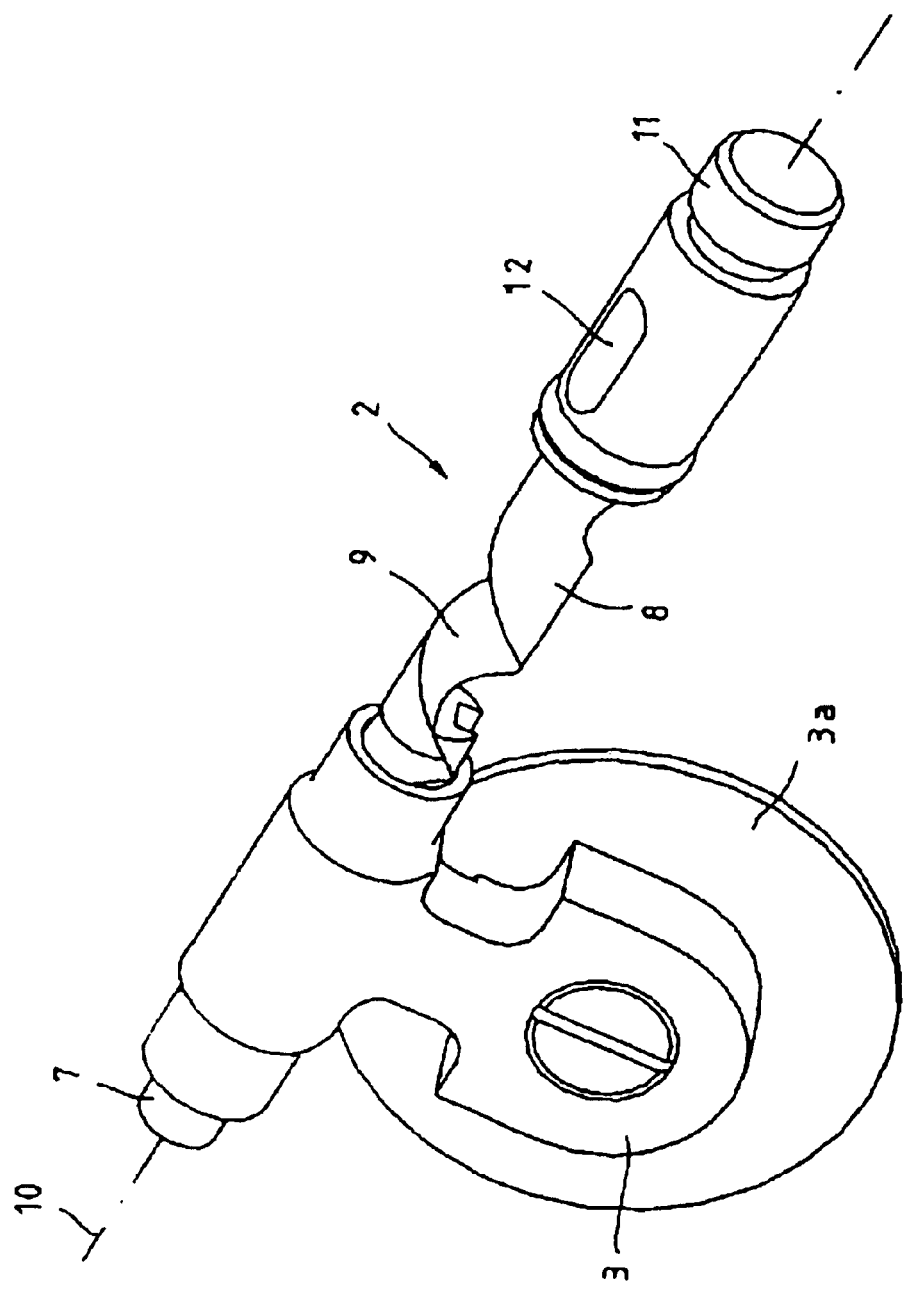
FIG. 4 shows a perspective view of the rotation axle with the valve body of the valve device mounted upon it, according to FIGS. 1 to 3.
Figure 5:
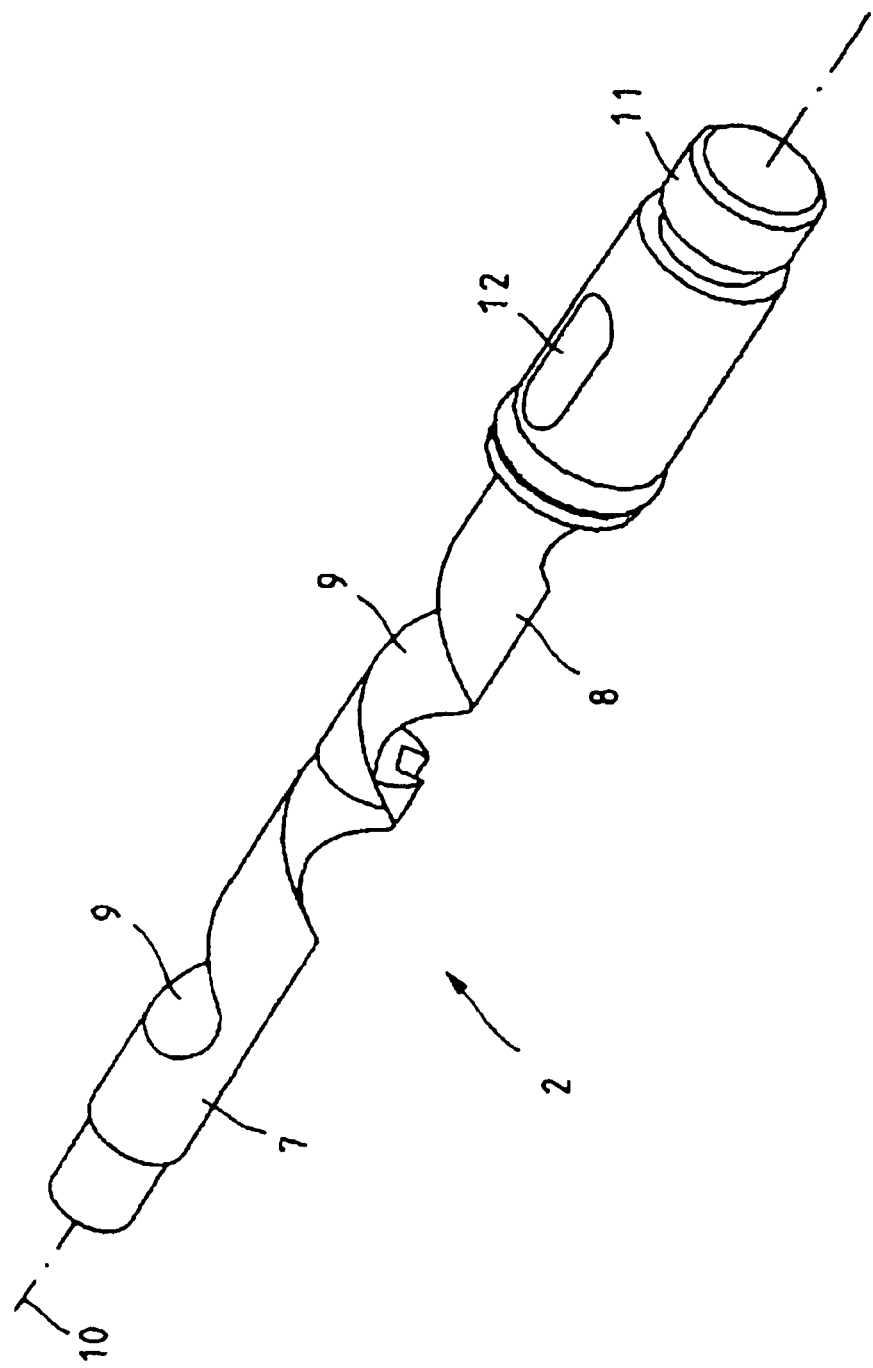
FIG. 5 shows a perspective view of the rotation axle according to FIG. 4 but without the valve body positioned on the rotation axle.
Figure 6:
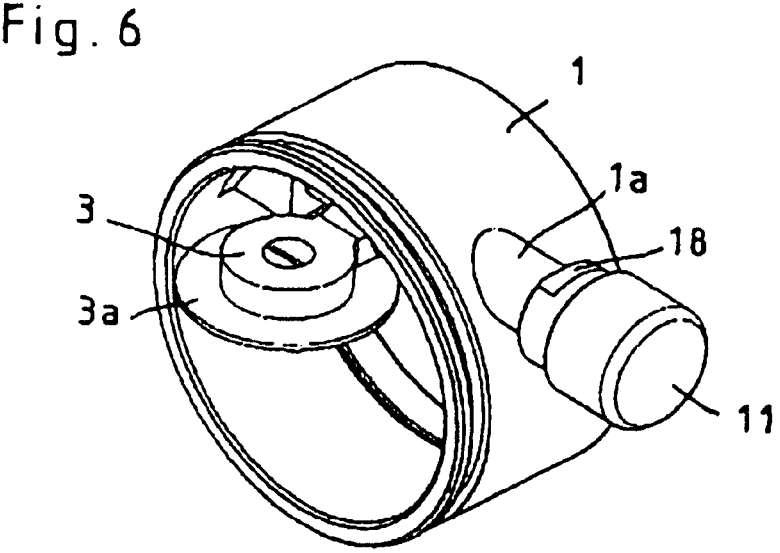
FIG. 6 shows a perspective view of a second embodiment of a valve device for medical instruments, according to the invention.
Figure 7:
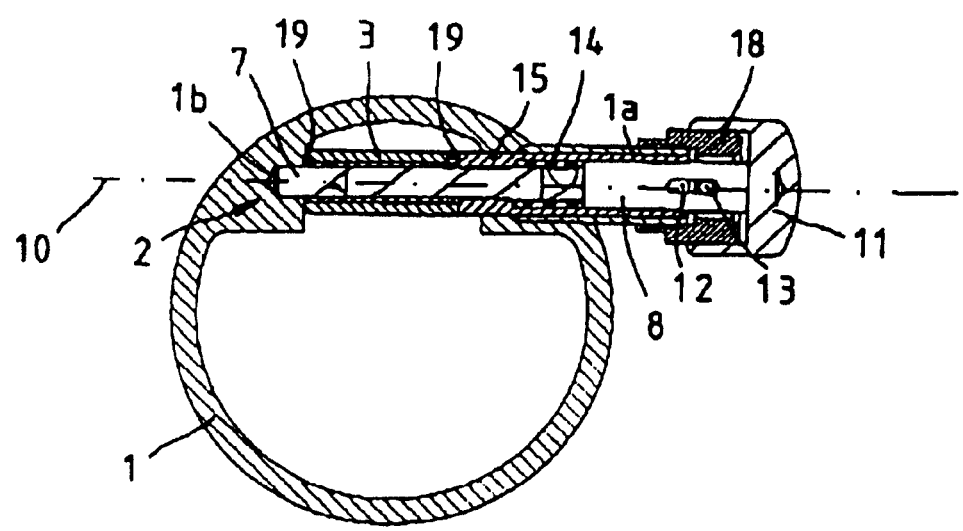
FIG. 7 shows a cut-out front view of the depiction according to FIG. 6.
Figure 8:
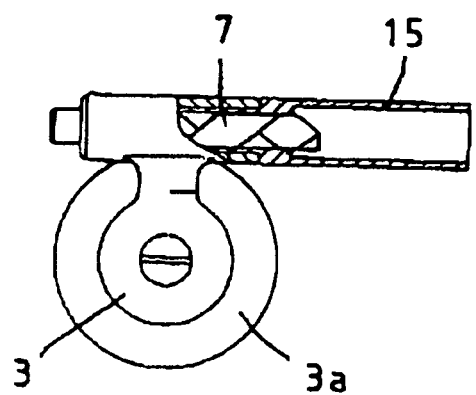
FIG. 8 shows a partly cut-out front view of the rotation axle with the valve body of the valve device mounted upon it, according to FIGS. 6 and 7.

The precise structure of the valve carrier unit 5 can be seen from FIGS. 2 through 8, which in particular make clear the structure and positioning of the rotation axle 2 in the housing 1, such that FIGS. 2 to 4 depict the configuration according to a first embodiment and FIGS. 6 to 8 depict the configuration according to a second embodiment.

As can be seen from FIGS. 2, 3 and FIGS. 7, 8 as well as the detailed views in FIGS. 4 and 5, the rotation axle 2 in the illustrated embodiment consists of two configured helical guide tracks 9 that can be connected with one another. The two components 7 and 8 of the rotation axle 2 here are mounted in the housing 1 in such a way that the component 7 carrying the valve body is positioned so that it can rotate exclusively around its longitudinal axis 10 and not cannot be displaced translationally, and the second component 8 is positioned so that it can slide axially exclusively in the longiudinal direction of the component 8 and cannot rotate in the housing 1.

Because, with instruments with especially sharp and/or sensitive points there is the danger that these points become blunted or even damaged upon puncturing the valve body 3 and, upon removal of pieces of tissue through the valve flap, to prevent the tissue sample from being damaged or being grazed by the forceps, it is possible to open the valve body 3 by means of a manually actuated mechanism.

In the illustrated embodiment this mechanism is configured as a push-button 11 that is in active connection with the component 8 of the rotation axle 2 can slide axially exclusively in the longitudinal direction and cannot rotate, and this button is positioned on the free end of a bearing bush connected firmly with the housing. To ensure that an actuation of the push-button 11 causes an exclusively axial sliding of the component 8 of the rotation axle 2, but not a radial rotation of the component 8 because of the mutual intertwining of the helical-shaped guide tracks 9 of the two components 7 and 8 of the rotation axle 2, in the area of the push-button 11 a guide pin 13 is provided, which is positioned in a recess 12 of the component 8 and blocks the component 8 against radial rotation.

As further shown from FIG. 3, the push-button 11 is pre-tensioned with respect to the axially slidable component 8 of the rotation axle 2 by means of at least one spring element in order, first, to prevent accidental opening of the valve body 3 and, second, to pre-tension the valve body 3 in the closed position.

The essential difference between the second embodiment of a valve device for medical instruments, illustrated in FIGS. 6 to 8, and the first embodiment, illustrated in FIGS. 2 to 4, consists in the fact that the two components 7 and 8 that form the rotation axle 2 in this second embodiment are mounted at least partly in an axle sleeve 15 that coaxially surrounds the rotation axle 2. The use of this axle sleeve 15 makes possible, first, a lateral guidance of the multi-partite rotation axle 2 and, in addition, facilitates the assembly and disassembly of the valve device by the configuration of component sets that can be pre-assembled, as is described more explicitly hereafter.

As can be seen in particular from FIGS. 7 and 8, in this embodiment of the valve device the valve body 3 configured here as a valve flap 3 is not positioned directly on the component 7 of the rotation axle 2 that can rotate exclusively around its longitudinal axis 10, but on the axis sleeve 15 that coaxially surrounds this component 7.

Figure 9:
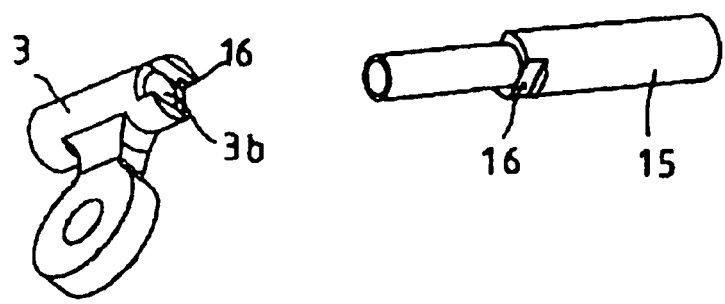
FIG. 9 shows a perspective view of the axle sleeve as well as the valve flap.

To ensure that rotation of the component 7 of the rotation axle 2 also causes a rotation of the valve body 3, in this embodiment of the configuration and mounting of the rotation axis, first, the component 7 of the rotation axle 2 that can rotate exclusively around its longitudinal axis 10 and the axle sleeve 15 are materially locked together and, second, the valve body 3 and the axle sleeve 15 are joined together by form-locking. As can be seen from FIG. 9, the form lock between the valve body 3 and the axle sleeve 15, for instance, can be obtained in that on the axle sleeve 15, first, and on the valve body 3 that is to be positioned on the axle sleeve 15, second, mutually corresponding mounting surfaces 16, for instance parallel flattened surfaces, are configured, ensuring that the rotation of the one component 3 or 15 always also causes a rotation of the other component 15 or 3.

Alternatively to these preferred types of connection for transmitting the rotary motion of the component 7 of the rotation axle 2 that can rotate exclusively around its longitudinal axis to the valve body 3 that is mounted on the axle sleeve 15, it is also possible of course to use all other combinations of means of connection such as form locking, material locking, and/or force locking.

The valve devices for medical instruments illustrated in FIGS. 1 to 9 operate as follows.

Starting from the closed position of the valve body 3 shown in FIGS. 1 to 3, in which the insulation surface 3a of the valve body 3 insulates the instrument and/or flow channel 4 against fluids, the valve body 3, positioned on the rotation axle 2 mounted in the housing 1, can rotate around the longitudinal axis 10 of the rotation axle 2 and can be moved into an open position that releases the instrument and/or flow channel 4, as is shown in FIG. 6. It is essential here for the mounting of the valve body 3, whether this body is mounted directly on the rotation axle 2 as in the first embodiment, or rather whether the valve body 3 is mounted indirectly, that is, by the interposition of the axle sleeve 15.

Moving the valve body 3 into the open position can occur in that a medical instrument is inserted in the direction of the arrow 17 in FIG. 1 into the instrument and/or flow channel 4 and this inserted medical instrument presses the valve body into the open position.

Just as with this mechanical opening of the valve device by a medical instrument inserted into the instrument and/or flow channel 4, the opening can occur through a fluid flow proceeding in the direction of the arrow 17 that is great enough to overcome the locking pressure of the spring element 14.

This rotation of the valve body 3, induced by a pressure force acting directly on the valve body 3, causes a turning of the component 7 of the rotation axle 2 that can rotate exclusively around the longitudinal axis 10, such that from the interlocking of the helical-shaped guide tracks 9 of the two components 7, 8 the turning of the component 7 necessarily causes an axial displacement of the component 8 that can slide exclusively axially, in this case a sliding to the left as illustrated in FIGS. 2, 3, and 7.

In addition to mounting the valve body 3 in the open position by forces that work directly on the valve body 3, it is possible to actuate the valve device by means of the manually actuated opening mechanism.

Pressing down the push-button 11 against the spring force of the spring element 14 causes a purely axial sliding of the component 8 of the rotation axle 2 in the direction of the component 7 of the rotation axle 2, because of the blocking by the guide pin 13. In the second embodiment, shown in FIGS. 6 and 7, the pre-tensioning force of the spring element 14 can be adjusted by a tension nut 18 that can be screwed onto the bearing bush 1a, so that with this embodiment the possibility exists of adjusting the pressure of the insulation in case of lack of insulation. The guide pin 13 to block the component 8 of the rotation axle 2 that can slide only axially is mounted in the tension nut 18 in the illustrated second embodiment.

Because of the arrangement of the valve body 3 between two mounting surfaces 19 in the housing 1 in the first embodiment and between one mounting surface 19 on the housing 1 and another mounting surface 19 on the axle sleeve 15 in the second embodiment, the component 7 of the rotation axle 2 cannot follow this axial sliding of the component 8, so that the pressing of the component 8 against the component 7 results in a rotation of the component 7, as well as of the valve body 3 that is positioned directly or indirectly on this component 7, around the longitudinal axis of the rotation axle, because of the intertwining helical-shaped guide tracks 9 and the longitudinally strong connection between the valve body 3 and the component 7 of the rotation axle 2.

As soon as a pressure force is exerted primarily on the push-button 11, the spring element 14 causes a sliding of the component 8 into the opposite direction, that is, away from the component 7 of the rotation axle 2. This sliding of the axially slidable component 8 then inevitably, by the coupling of the helical guide tracks 9, causes a rotation of the component 7 and thus of the valve body 3 back into the closed position.

Assembly of the second embodiment of a valve device for medical instruments, depicted in FIGS. 6 through 9, occurs as follows:

It is advantageous for the valve device according to the second embodiment that individual components can be combined to form pre-fabricated component groups, so that the assembly and disassembly can be clearly simplified.

Before the final assembly of the complete valve device, the component 7 of the rotation axle 2 that can rotate exclusively around the longitudinal axis 10 is first inserted into the axle sleeve 15 and is materially locked with it, for instance by soldering. Then the valve body 3 is equipped with the insulation surface that is configured as a flat insulation. To complete the rotation axle 2, now the spring element that is configured as a pressure spring as well as the component 8 of the rotation axle 2 that can slide only axially is inserted into the axle sleeve 15 which is already provided with the component 7 of the rotation axle 2.

Then the prefabricated valve body 3 is inserted into the valve housing 1 in such a way that the bore-hole 3b is flush, first, with the bearing bush 1a and, second, with a mounting bore-hole 1b in the housing 1, for insertion of the axis sleeve 15. Now the axle sleeve 15 together with the prefabricated rotation axle 2 can be inserted into the bore-hole 3b of the valve body 3 through the free end of the bush bearing 1a, until the free end of the component 7 settles in the mounting bore-hole 1b.

To adjust the pre-tensioning of the spring element 1, now the tension nut 18 is screwed onto the bearing bush 1a and the push-button 11 is mounted on the free end of the component 8 of the rotation axle 2 that extends beyond the free and of the bearing bush 1a, by which pressure can be exerted on the spring element 14. After adjustment of the desired pre-tensioning of the spring element 14, which can occur during assembly and in particular also after assembly, for instance for removing uninsulated spots, the guide pin 13 that fastens the component 8 to prevent rotation is inserted into the tension nut 8 and the recess 12 of the component 8 of the rotation axle 2.

A valve device configured in this manner is distinguished by its simple structure, consisting of only few components, a structure that allows reliable insulation performance along with easy and rapid assembly and disassembly of the valve device, for instance for cleaning purposes.

What is claimed is:

1. A valve device for medical instruments, in particular trocars, having a valve body configured as a flap for opening and closing an instrument and/or flow channel, which is positioned on a rotation axle mounted in a housing, characterized in that the rotation axle is of multi-part construction, such that the individual components of the rotation axle are rod-shaped and are directly connected with one another by intertwining helical-shaped guide tracks which are configured on the outer surface of each rod-shaped component to be connected.

2. A valve device according to claim 1, characterized in that one component of the rotation axle is positioned so that it can rotate exclusively around its longitudinal axis in the housing.

3. A valve device according to claim 2, characterized in that the rotation axle consists of two components, such that one component is mounted so that it can rotate exclusively around its longitudinal axis in the housing and the other component is mounted so that it can slide axially in the housing exclusively in the longitudinal direction of the component.

4. A valve device according to claim 2, characterized in that the valve body is mounted on the component of the rotation axle that can rotate exclusively around its longitudinal axis.

5. A valve device according to claim 1, characterized in that the rotation axle is mounted at least partly in an axle sleeve.

6. A valve device according to claim 5, characterized in that the valve body is mounted on the axle sleeve.

7. A valve device according to claim 6, characterized in that the valve body and the axle sleeve are in an essentially form-locking connection to one another.

8. A valve device according to claim 6, characterized in that the component that can rotate exclusively around its longitudinal axis and the axle sleeve are in a material-locking connection to one another.

9. A valve device according to claim 1, characterized in that the valve body mounted on the rotation axle can be displaced into the open position by a manually actuated mechanism.

10. A valve device according to claim 9, characterized in that the rotation axle consists of two components, such that one component is mounted so that it can slide axially in the housing exclusively in the longitudinal direction of the component and the other component is mounted so that it can rotate exclusively around its longitudinal axis in the housing, and characterized in that the manually actuated mechanism is configured as a push-button that is in active connection with the component of the rotation axle that is mounted so that it can slide axially exclusively in the longitudinal direction.

11. A valve device according to claim 10, characterized in that the push-button is pre-tensioned by at least one spring element with respect to the axially slidable component of the rotation axle.

12. A valve device according to claim 11, characterized in that the valve body is pre-tensioned by the at least one spring element in the direction of the closed position.

13. A valve device according to claim 11, characterized in that the pre-tensioning of the at least one spring element can be adjusted by means of a tension nut that can be screwed onto a bearing bush of the housing in the area of the manually actuated mechanism.

14. A valve device according to claim 13, characterized in that the component of the rotation axle mounted so that it can slide axially exclusively in the longitudinal direction is ensured against rotation by a guide pin.

15. A valve device according to claim 14, characterized in that the guide pin in the area of the manually actuated mechanism is mounted in a recess in the axially slidable component of the rotation axle.

16. A valve device according to claim 14, characterized in that the guide pin is mounted in the tension nut.

17. A valve device according to claim 1, characterized in that the housing component that bears the valve body as well as the rotation axle forms a separate valve carrier unit.

* * * * *